(12) United States Patent
Zhang et al.

(10) Patent No.: US 9,169,268 B2
(45) Date of Patent: Oct. 27, 2015

(54) USE OF 7-ALKOXY FANGCHINOLINE COMPOUNDS IN PREVENTING, ALLEVIATING AND/OR TREATING DEPRESSION

(71) Applicant: Peking University, Beijing (CN)

(72) Inventors: Yonghe Zhang, Beijing (CN); Xueqiong Zhang, Beijing (CN); Zhaofu Sheng, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 14/507,584

(22) Filed: Oct. 6, 2014

(65) Prior Publication Data
US 2015/0025099 A1 Jan. 22, 2015

Related U.S. Application Data

(63) Continuation-in-part of application No. PCT/CN2012/084998, filed on Nov. 22, 2012.

(30) Foreign Application Priority Data

Apr. 6, 2012 (CN) .......................... 2012 1 0099615

(51) Int. Cl.
*A61K 31/47* (2006.01)
*C07D 323/00* (2006.01)
*C07D 498/16* (2006.01)
*A61K 31/4748* (2006.01)

(52) U.S. Cl.
CPC .......... *C07D 498/16* (2013.01); *A61K 31/4748* (2013.01)

(58) Field of Classification Search
CPC .......................... C07D 498/16; A61K 31/4748
USPC ...................... 514/308, 279; 549/348; 546/37
See application file for complete search history.

(56) References Cited

U.S. PATENT DOCUMENTS 6,617,335 B1 * 9/2003 Wang et al. ................... 514/308

FOREIGN PATENT DOCUMENTS

CN 102274227 * 12/2011

* cited by examiner

*Primary Examiner* — T. Victor Oh
(74) *Attorney, Agent, or Firm* — Polsinelli PC; Andrea Porterfield (57) ABSTRACT

The present invention provides a method of preventing, alleviating and/or treating depression, comprising the step of administering to a subject in need thereof a therapeutically effective amount of a 7-alkoxy fangchinoline compound or a pharmaceutically acceptable derivative thereof.

15 Claims, 5 Drawing Sheets

USE OF 7-ALKOXY FANGCHINOLINE COMPOUNDS IN PREVENTING, ALLEVIATING AND/OR TREATING DEPRESSION

CROSS REFERENCE TO RELATED APPLICATIONS

This application is a continuation-in-part of International Patent Application No. PCT/CN2012/084998, filed on Nov. 22, 2012, which in turn claims the benefit and priority of Chinese Patent Application No. 201210099615.5, filed on Apr. 6, 2012. The entire contents of all applications are incorporated herein by reference in their entireties.

FIELD OF THE INVENTION

The present invention relates to use of 7-alkoxy fangchinoline compounds in preventing, alleviating and/or treating depression.

TECHNICAL FIELD

Chinese Patent Publication No. CN102274227A disclosed the use of tetrandrine (TET in the preparation of a medicament for preventing, alleviating and/or treating depression. Depression is a clinically common mood disorder and the incidence rate thereof is increasing. Abnormal enhancement of GSK-3β activity is believed to be highly relevant to the pathogenesis of depression or schizophrenia and to the therapeutic mechanism of anti-depression or anti-schizophrenic drugs. There is an urgent need to develop a novel anti-depression drug suitable for clinical treatment.

SUMMARY OF THE INVENTION

In one aspect, the present invention provides a method of preventing, alleviating and/or treating depression, comprising the step of administering to a subject in need thereof a therapeutically effective amount of a compound of formula (I) or a pharmaceutically acceptable derivative thereof, formula (I)

wherein, $R_1$ is an alkyl of general formula $-C_nH_{2n+1}$, and n is an integer greater than or equal to 1; $R_2$ is selected from the group consisting of hydrogen, methyl, ethyl, propyl, isopropyl, butyl, isobutyl and acyl; $X_1$, $X_2$, $X_3$ and $X_4$ may be the same or different, and each independently represent hydrogen, fluorine, chlorine, bromine, iodine, nitro, hydroxyl or methoxy; and when n is 1, $X_1$, $X_2$, $X_3$ and $X_4$ may not all be hydrogen.

The present invention also provides a method of alleviating and/or treating schizophrenia, comprising the step of administering to a subject in need thereof a therapeutically effective amount of a compound of formula (I) or a pharmaceutically acceptable derivative thereof as defined above.

The term "pharmaceutically acceptable derivative" as used herein includes a pharmaceutically acceptable salt, ester, ether, solvate, hydrate, stereoisomer or prodrug of a compound of formula (I). In the meantime, stereoisomers in which C(1) and C(1') are RR, SS, 1S1'R and 1R1'S configurations are included.

The term "therapeutically effective amount" as used herein refers to an amount of the therapeutic agent sufficient to result in a desired biological or medical response in a subject as expected by a clinical physician. The "therapeutically effective amount" of a compound of the present invention may be determined by a skilled artisan in consideration of factors such as administration route, weight and age of the subject, and disease condition. For example, a typical daily dose may range from 0.01 mg/kg to 100 mg/kg of the therapeutic agent. In other embodiments, the daily dose may range from about 0.01 mg/kg to about 1.0 mg/kg, from about 0.8 mg/kg to about 10 mg/kg, from about 8.0 mg/kg to about 30 mg/kg, from about 25 mg/kg to about 50 mg/kg, from 45 mg/kg to about 70 mg/kg, or from 65 mg/kg to about 100 mg/kg.

In clinical practice, the compound of the present invention may be administered by any conventional route, e.g. orally or parenterally. The compound of the present invention may be formulated into any suitable dosage form, e.g. tablet, powder, capsule, or injection.

In some embodiments of the present invention, $R_1$ is methyl, and at least one of $X_1$, $X_2$, $X_3$ and $X_4$ represents fluorine, chlorine, bromine, iodine or nitro. In some embodiments, $R_1$ is methyl, and $X_1$ and $X_3$ each independently represent chlorine or bromine. In some embodiments, $R_1$ is methyl, and $X_1$ and $X_3$ are the same and represent chlorine or bromine. Preferably, $R_2$ is methyl.

In some preferred embodiments of the present invention, compound of formula (I) is selected from the group consisting of 5-chloro-7-methoxy fangchinoline (Compound 1), 5,14-dibromo-7-methoxy fangchinoline (Compound 2), 7-ethoxy fangchinoline (Compound 3, also referred to as YH-200), 5-bromo-7-ethoxy fangchinoline (Compound 4), 5,14-dibromo-7-ethoxy fangchinoline (Compound 5), 7-propoxy fangchinoline (Compound 6), 7-butoxy fangchinoline (Compound 7), 7-isopropoxy fangchinoline (Compound 8), and any combinations thereof.

In another aspect, the present invention provides a compound of formula (I) or a pharmaceutically acceptable derivative thereof, formula (I)

wherein, $R_1$ is ethyl; $R_2$ is methyl; $X_1$, $X_2$, $X_3$ and $X_4$ may be the same or different, and each independently represent hydrogen, fluorine, chlorine, bromine, iodine, nitro, hydroxyl or methoxy.

In some embodiments of the present invention, $X_1$ and $X_3$ each independently represent fluorine, chlorine, bromine, iodine or nitro. In some embodiments, $X_1$ and $X_3$ each independently represent chlorine or bromine. In some embodiments, $X_1$ and $X_3$ are the same and represent chlorine or bromine.

In some preferred embodiments of the present invention, compound of formula (I) is selected from the group consisting of 5-bromo-7-ethoxy fangchinoline (Compound 4) and 5,14-dibromo-7-ethoxy fangchinoline (Compound 5).

The 7-alkoxy fangchinoline compound of formula (I) or a pharmaceutically acceptable derivative thereof may be used alone or in combination with other anti-mental disorder medicament or adjuvant therapeutic medicament for treating and/or alleviating depressive symptoms.

DETAILED DESCRIPTION OF EMBODIMENTS

Compounds 1-8 of the present invention are as follows.

Compound 1. 5-chloro-7-methoxy fangchinoline (Berbaman, 5-chloro-6,6',7,12-tetramethoxy-2,2'-dimethyl-). ESI-MS (m/z): 658.25 (M+1). $C_{38}H_{41}N_2O_6Cl$. $^1$H NMR (300 MHz, CDCl$_3$) δ: 2.31 (s, 3H, NCH$_3$), 2.70 (s, 3H, NCH$_3$), 3.23 (s, 3H, OCH$_3$), 3.38 (s, 3H, OCH$_3$), 3.76 (s, 3H, OCH$_3$), 3.92 (s, 3H, OCH$_3$), 6.05~7.34 (m, 9H, aromatic hydrocarbon H).

Compound 2. 5,14-dibromo-7-methoxy fangchinoline (Berbaman, 5,14-dibromo-6,6',7,12-tetramethoxy-2,2'-dimethyl-). An acicular crystal (Methanol), mp: 187-189° C. ESI-MS (m/z): 781.2 (M+1), $C_{38}H_{40}N_2O_6Br_2$. $^1$H NMR (300 MHz, CDCl$_3$) δ: 2.27 (s, 3H, NCH$_3$), 2.65 (s, 3H, NCH$_3$), 3.24 (s, 3H, OCH$_3$), 3.38 (s, 3H, OCH$_3$), 3.74 (s, 3H, OCH$_3$), 3.89 (s, 3H, OCH$_3$), 2.44-3.96 (m, 14H, alkane H), 6.02 (s, 1H, aromatic hydrocarbon H), 6.34 (dd, J=9.0, 2.3 Hz, 1H, aromatic hydrocarbon H), 6.53 (s, 1H, aromatic hydrocarbon H), 6.60 (s, 1H, aromatic hydrocarbon H), 6.84 (dd, J=10.0, 2.7 Hz, 1H, aromatic hydrocarbon H), 7.05 (dd, J=10.0, 2.7 Hz, 1H, aromatic hydrocarbon H), 7.07 (s, 1H, aromatic hydrocarbon H), 7.34 (dd, J=9.0, 2.3 Hz, 1H, aromatic hydrocarbon H).

Compound 3. 7-ethoxy fangchinoline (Berbaman, 6,6',12-trimethoxy-7-ethoxy-2,2'-dimethyl) (also referred to as YH-200). A colorless acicular crystal (Ethanol), mp: 109.5-111.° C. ESI-MS (m/z): 637.33 (M+1), $C_{39}H_{44}N_2O_6$. $^1$H NMR (300 MHz, CDCl$_3$) δ: 0.80 (t, 3H, OCH$_2$CH$_3$), 2.32 (s, 3H, NCH$_3$), 2.58 (s, 3H, NCH3), 2.40~3.80 (m, 16H, alkane H), 3.37 (s, 3H, OCH3), 3.74 (s, 3H, OCH3), 3.93 (s, 3H, OCH$_3$), 5.95 (s, 1H, aromatic hydrocarbon H), 6.30 (s, 1H, aromatic hydrocarbon H), 6.32 (dd, J=9.2, 2.1 Hz, 1H, aromatic hydrocarbon H), 6.50 (s, 1H, aromatic hydrocarbon H), 6.52 (dd, J=10.2, 2.2 Hz, 1H, aromatic hydrocarbon H), 6.81 (dd, J=9.2, 2.1 Hz, 1H, aromatic hydrocarbon H), 6.83 (s, 1H, aromatic hydrocarbon H), 6.87 (dd, J=10.2, 2.2 Hz, 1H, aromatic hydrocarbon H), 7.14 (s, (dd, J=9.0, 1.0 Hz, 1H, aromatic hydrocarbon H), 7.36 (dd, J=9.0, 1.0 Hz, 1H, aromatic hydrocarbon H).

Compound 4. 5-bromo-7-ethoxy fangchinoline (Berbaman, 5-bromo-6,6',12-tetramethoxy-7-ethoxy-2,2'-dimethyl-). An acicular crystal (Methanol-Diethyl ether), mp: 146-148° C. ESI-MS (m/z): 716.24 (M+1), $C_{39}H_{43}N_2O_6Br$. $^1$H NMR (300 MHz, CDCl$_3$) δ: 0.81 (t, 3H, OCH$_2$CH$_3$), 2.32 (s, 3H, NCH$_3$), 2.60 (s, 3H, NCH$_3$), 2.40~3.80 (m, 16H, alkane H), 3.39 (s, 3H, OCH$_3$), 3.72 (s, 3H, OCH$_3$), 3.92 (s, 3H, OCH$_3$), 6.03~7.35 (m, 9H, aromatic hydrocarbon H).

Compound 5. 5,14-dibromo-7-ethoxy fangchinoline (Berbaman, 5,14-dibromo-6,6',7,12-tetramethoxy-2,2'-dimethyl-). An acicular crystal (Methanol), mp: 186-188° C. ESI-MS (m/z): 795.26 (M+1), $C_{39}H_{42}N_2O_6Br_2$. $^1$H NMR (300 MHz, CDCl$_3$) δ: 0.80 (t, 3H, OCH$_2$CH$_3$), 2.28 (s, 3H, NCH$_3$), 2.69 (s, 3H, NCH$_3$), 3.38 (s, 3H, OCH$_3$), 3.73 (s, 3H, OCH$_3$), 3.89 (s, 3H, OCH$_3$), 2.44-3.96 (m, 16H, alkane H), 6.02 (s, 1H, aromatic hydrocarbon H), 6.33 (dd, J=9.0, 2.3 Hz, 1H, aromatic hydrocarbon H), 6.54 (s, 1H, aromatic hydrocarbon H), 6.60 (s, 1H, aromatic hydrocarbon H), 6.83 (dd, J=10.0, 2.7 Hz, 1H, aromatic hydrocarbon H), 7.04 (dd, J=10.0, 2.7 Hz, 1H, aromatic hydrocarbon H), 7.06 (s, 1H, aromatic hydrocarbon H), 7.34 (dd, J=9.0, 2.3 Hz, 1H, aromatic hydrocarbon H).

Compound 6. 7-propoxy fangchinoline (Berbaman, 6,6',12-trimethoxy-7-propoxy-2,2'-dimethyl-). An acicular crystal (MeOH), mp: 174.8-176.3; ESI-MS (m/z): 651.35 (M+1), $C_{40}H_{46}N_2O_6$. $^1$H NMR (300 MHz, CDCl$_3$) δ: 0.79 (t, 3H, OCH$_2$CH$_2$CH$_3$), 2.32 (s, 3H, NCH$_3$), 2.58 (s, 3H, NCH3), 2.40~3.81 (m, 18H, alkane H), 3.37 (s, 3H, OCH3), 3.73 (s, 3H, OCH3), 3.92 (s, 3H, OCH$_3$), 5.94~7.36 (m, 10H, aromatic hydrocarbon H).

Compound 7. 7-butoxy fangchinoline (Berbaman, 6,6',12-trimethoxy-7-butoxy-2,2'-dimethyl-). A columnar crystal (MeOH); mp: 155-156° C.; ESI-MS (m/z): 665.38 (M+1), $C_{41}H_{48}N_2O_6$. $^1$H NMR (300 MHz, CDCl$_3$) δ: 0.78 (t, 3H, OCH$_2$CH$_2$CH$_2$CH$_3$), 1.13~3.60 (m, 20H, alkane H), 2.32 (s, 3H, NCH$_3$), 2.59 (s, 3H, NCH$_3$), 3.36 (s, 3H, OCH$_3$), 3.73 (s, 3H$_2$OCH$_3$), 3.92 (s, 3H, OCH$_3$), 5.94~7.36 (m, 10H, aromatic hydrocarbon H).

Compound 8. 7-isopropoxy fangchinoline (Berbaman, 6,6',12-trimethoxy-7-isopropoxy-2,2'-dimethyl-). ESI-MS (m/z): 651.34 (M+1); $C_{40}H_{46}N_2O_6$. $^1$H NMR (300 MHz, CDCl$_3$) δ: 0.76[d, 6H, OCH(CH$_3$)$_2$], 2.34 (s, 3H, NCH$_3$), 2.62 (s, 3H, NCH$_3$), 2.40~3.60 (m, 15H, alkane H), 3.34 (s, 3H, OCH$_3$), 3.71 (s, 3H, OCH$_3$), 3.92 (s, 3H, OCH$_3$), 5.86~7.38 (m, 10H, aromatic hydrocarbon H).

EXAMPLES

The present invention will be further illustrated with reference to the following experiments, taking compounds 1-8 as examples. The invention, however, should not be limited to any of the details in these examples.

Example 1

GSK-3β Activity Assay

The GSK-3β phosphorylation level was determined by using a Z'-LYTE assay (Life Technologies). The assay was performed in a 384-well plate. The wells of the testing plate were divided into blank control wells (without the enzyme), enzyme control wells (without the testing substance), and testing wells (with the enzyme and the testing substance at various concentrations). The inhibition rate of the testing substance is expressed as: inhibition %=(E−S)/(E−B)×100, wherein E is the average emission ratio of enzyme control wells; B is the average emission ratio of blank control wells; S is the emission ratio of the testing sample wells. The median effective concentration of each compound ($EC_{50}$ μM) was calculated by using the resultant inhibition rate of each sample at various concentrations.

TABLE 1

$EC_{50}$ in the inhibition of GSK-3β activity (n = 3)

| Compounds | Mean $EC_{50}$ (μM) |
|---|---|
| Compound 1 (5-chloro-7-methoxy fangchinoline) | 3.21 |
| Compound 2 (5,14-dibromo-7-methoxy fangchinoline) | 2.01 |
| Compound 3 (7-ethoxy fangchinoline, YH-200) | 0.86 |
| Compound 4 (5-bromo-7-ethoxy fangchinoline) | 1.22 |
| Compound 5 (5,14-dibromo-7-ethoxy fangchinoline) | 1.26 |
| Compound 6 (7-propoxy fangchinoline) | 1.68 |
| Compound 7 (7-butoxy fangchinoline) | 2.33 |
| Compound 8 (7-isopropoxy fangchinoline) | 1.35 |
| tetrandrine (7-methoxy fangchinoline) | 9.02 |
| 5,7-dimethoxy-fangchinoline | >10 |
| berbamine (12-desmethyltetrandrine) | >10 |
| 12-acetoxyberbamine | >10 |
| 12-(4-ethoxy)-butoxyberbamine | >10 |

It was demonstrated by the study that compounds 1-8 of the present invention all exhibited a high inhibition effect against GSK-3β activity ($EC_{50}$<3.5 μM) (see, Table 1). As compared with tetrandrine (TET), 5,7-dimethoxy-fangchinoline, berbamine (12-desmethyltetrandrine) and 12-acetoxy berbamine, compounds 1-8 had a 3-10 times lower median effective concentration ($EC_{50}$), indicating an evident potency advantage.

The results suggested that compounds 1-8 all had potency for treating schizophrenia and depression disorders that are associated with abnormally elevated GSK-3β activity.

Example 2

The ameliorating/therapeutic effect of compounds 1-8 on depression behaviors in a chronic unpredictable stress (CUS) model in rats, in comparison with tetrandrine, 5,7-dimethoxy-fangchinoline, berbamine, 12-acetoxyberbamine and 12-(4-ethoxy)-butoxyberbamine.

The chronic unpredictable stress model is usually used as a depression model. The experimental method is as follows. Stimulation includes forced swimming (10° C., 6 min), tail clamping (1 cm from the tail tip, 1 min), water deprivation (24 h), fasting (24 h), isolated housing (24 h), tail suspension (1 h), immobility (2 h), high-speed horizontal oscillation (120 times/min, 1 h), foot shock for 45 minutes (mean 1 mA, time course 1 s, once/min). These stressors were randomly scheduled over a one-week period and repeated throughout the 23-day experiment. The non-stress control group was housed under normal conditions. Time: between 9:00 a.m. and 2:00 p.m. Since Day 15, the animals in each group were daily intragastrically administered with the subject medicament and double distilled water based on body weight (blank group and CUS model group) respectively, 60 minutes before the stress. Imipramine (intraperitoneally, IP) was adopted as a positive control. Behavior and sleep electroencephalogram analyses were carried out on Day 22-23 of the stress. On Day 21, 60 minutes after the final administration, a sucrose solution intake test was carried out and sleep electroencephalogram was recorded simultaneously. On Day 22, EPM and forced swimming tests were carried out.

TABLE 2

The influence of the compounds of formula (I) on forced swimming, sucrose solution preference and autonomous mobility in a chronic unpredictable stress model in rats (means ± SEM, n = 10)

| Groups | Forced swimming Immobility time (seconds) | Sucrose solution preference (%) | Autonomous movement | |
|---|---|---|---|---|
| | | | Distance (mm) | Speed (mm/second) |
| Blank control group | 57.4 ± 4.5 | 100 | 14870.12 ± 1187.70 | 49.57 ± 3.96 |
| CUS model group | 180.8 ± 6.3** | 51.6 ± 3.1** | 1097.52 ± 716.52** | 3.66 ± 2.39** |
| Model group + compound 1 | | | | |
| 7.50 mg/kg | 157.4 ± 5.6##,$$ | 69.6 ± 4.6## | 7581.17 ± 845.04##,$$ | 25.27 ± 2.38##,$$ |
| 15.0 mg/kg | 99.2 ± 2.9##,$$ | 78.8 ± 4.0##,$$ | 9518.08 ± 704.12##,$$ | 31.73 ± 3.44##,$$ |
| 30.0 mg/kg | 76.6 ± 4.7##,$$ | 81.6 ± 3.7##,$$ | 10347.64 ± 923.01##,$$ | 34.49 ± 3.75##,$$ |
| Model group + compound 2 | | | | |
| 7.50 mg/kg | 136.2 ± 4.6##,$$ | 72.5 ± 3.0## | 9031.41 ± 639.33##,$$ | 30.10 ± 3.88##,$$ |
| 15.0 mg/kg | 96.7 ± 4.5##,$$ | 89.0 ± 4.6##,$$ | 10116.74 ± 746.48##,$$ | 33.72 ± 4.02##,$$ |
| 30.0 mg/kg | 76.8 ± 3.4##,$$ | 88.5 ± 3.1##,$$ | 12062.32 ± 903.42##,$$ | 40.21 ± 5.36##,$$ |
| Model group + compound 3 | | | | |
| 7.50 mg/kg | 120.6 ± 6.4##,$$ | 82.3 ± 3.3##,$$ | 13612.65 ± 792.22##,$$ | 45.38 ± 2.64##,$$ |
| 15.0 mg/kg | 88.5 ± 4.3##,$$ | 93.6 ± 4.6##,$$ | 14409.83 ± 664.54##,$$ | 48.03 ± 4.02##,$$ |
| 30.0 mg/kg | 58.7 ± 5.2##,$$ | 98.1 ± 3.7##,$$ | 14636.14 ± 812.31##,$$ | 48.78 ± 5.36##,$$ |

TABLE 2-continued

The influence of the compounds of formula (I) on forced swimming, sucrose solution preference and autonomous mobility in a chronic unpredictable stress model in rats (means ± SEM, n = 10)

| Groups | Forced swimming Immobility time (seconds) | Sucrose solution preference (%) | Autonomous movement | |
|---|---|---|---|---|
| | | | Distance (mm) | Speed (mm/second) |
| Model group + compound 4 | | | | |
| 7.50 mg/kg | 134.3 ± 4.4##,$$ | 79.2 ± 3.4##,$$ | 13257.21 ± 756.36##,$$ | 44.19 ± 2.64##,$$ |
| 15.0 mg/kg | 96.1 ± 3.74##,$$ | 81.5 ± 4.7##,$$ | 13615.71 ± 743.43##,$$ | 45.39 ± 4.02##,$$ |
| 30.0 mg/kg | 60.5 ± 5.3##,$$ | 93.6 ± 3.2##,$$ | 14362.26 ± 771.52##,$$ | 47.87 ± 5.36##,$$ |
| Model group + compound 5 | | | | |
| 7.50 mg/kg | 144.4 ± 4.0##,$$ | 84.1 ± 3.3## | 13732.42 ± 732.45##,$$ | 45.77 ± 2.64##,$$ |
| 15.0 mg/kg | 99.6 ± 3.7##,$$ | 86.0 ± 3.5##,$$ | 14003.63 ± 737.47##,$$ | 46.68 ± 4.02##,$$ |
| 30.0 mg/kg | 69.7 ± 4.8##,$$ | 91.5 ± 4.2##,$$ | 14561.84 ± 807.52##,$$ | 48.54 ± 5.36##,$$ |
| Model group + compound 6 | | | | |
| 7.5 mg/kg | 134.6 ± 5.2##,$$ | 79.45 ± 3.3## | 8940.78 ± 714.35##,$$ | 29.80 ± 2.64##,$$ |
| 15 mg/kg | 98.8 ± 4.7##,$$ | 85.5 ± 3.6##,$$ | 11574.92 ± 732.36##,$$ | 38.58 ± 3.02##,$$ |
| 30 mg/kg | 78.5 ± 3.9##,$$ | 90.4 ± 4.3##,$$ | 12566.27 ± 764.42##,$$ | 41.89 ± 4.36##,$$ |
| Model group + compound 7 | | | | |
| 7.5 mg/kg | 142.2 ± 6.0##,$$ | 70.7 ± 4.1## | 8823.36 ± 673.14##,$$ | 29.41 ± 2.64##,$$ |
| 15 mg/kg | 94.4 ± 5.3##,$$ | 87.1 ± 3.5## | 9586.43 ± 756.75##,$$ | 31.95 ± 4.02##,$$ |
| 30 mg/kg | 81.3 ± 4.3##,$$ | 86.3 ± 3.4##,$$ | 11768.25 ± 903.41##,$$ | 39.23 ± 5.36##,$$ |
| Model group + compound 8 | | | | |
| 7.5 mg/kg | 136.5 ± 5.8##,$$ | 80.5 ± 3.6## | 9968.41 ± 965.52##,$$ | 33.22 ± 2.64##,$$ |
| 15 mg/kg | 102.3 ± 6.2##,$$ | 84.7 ± 3.2##,$ | 12194.23 ± 887.65##,$$ | 40.64 ± 4.02##,$$ |
| 30 mg/kg | 72.4 ± 5.5##,$$ | 90.1 ± 3.8##,$$ | 13053.78 ± 1005.46##,$$ | 43.51 ± 5.36##,$$ |
| Model group + tetrandrine | | | | |
| 7.5 mg/kg | 179.5 ± 8.3 | 55.4 ± 3.2 | 1369.54 ± 532.47 | 4.57 ± 1.85 |
| 15 mg/kg | 175.3 ± 8.8 | 52.9 ± 3.7 | 1124.37 ± 504.85 | 3.75 ± 1.98 |
| 30 mg/kg | 162.7 ± 8.5# | 67.7 ± 3.3# | 1027.36 ± 456.76 | 3.42 ± 1.33 |
| 60 mg/kg | 160.8 ± 7.6## | 70.2 ± 4.6## | 1285.41 ± 401.24 | 4.28 ± 1.56 |
| Model group + 5,7-dimethoxyfangchinoline | | | | |
| 30 mg/kg | 179.1 ± 6.8 | 53.7 ± 4.8 | 1189.64 ± 315.84 | 3.97 ± 1.48 |
| 60 mg/kg | 168.3 ± 5.2 | 55.3 ± 4.2 | 936.47 ± 366.32 | 3.12 ± 1.42 |
| Model group + berbamine | | | | |
| 30 mg/kg | 179.2 ± 6.2 | 55.05 ± 3.06 | 1387.56 ± 584.24 | 4.63 ± 1.49 |
| 60 mg/kg | 175.8 ± 7.5 | 49.56 ± 4.27 | 1053.45 ± 476.33 | 3.51 ± 1.65 |
| Model group + 2-acetoxyberbamine | | | | |
| 30 mg/kg | 179.2 ± 6.6 | 54.29 ± 3.74 | 984.41 ± 542.67 | 3.28 ± 1.35 |
| 60 mg/kg | 169.9 ± 7.4 | 53.34 ± 3.04 | 1135.49 ± 575.54 | 3.78 ± 1.46 |
| Model group + 12-(4-ethoxy)-butoxy-berbamine | | | | |
| 30 mg/kg | 179.5 ± 6.3 | 54.19 ± 4.45 | 1367.52 ± 683.88 | 4.56 ± 1.74 |
| 60 mg/kg | 175.3 ± 8.4 | 53.27 ± 3.55 | 935.73 ± 586.51 | 3.12 ± 1.31 |
| Imipramine 40 mg/kg | 58.3 ± 3.8##,$$ | 68.4 ± 5.3# | 12483.88 ± 1142.77##,$$ | 41.62 ± 3.81##,$$ |

**P < 0.01 as compared with control group;
P < 0.05,
P < 0.01 as compared with CUS group;
$P < 0.05,
$$P < 0.01 as compared with tetrandrine 60 mg/kg group.
The data were analyzed by one-way analysis of variance (ANOVA) followed by post hoc Student-Newman-Keuls test for multiple comparisons, and the sucrose preference test was analyzed by two-way repeated measures ANOVA (one factor repetition).

Result 1: As shown in Table 2, compounds 1-8, intragastrically administered for consecutive 7 days at doses of 7.5, 15 and 30 mg/kg, could all evidently ameliorate depression-like behaviors in a CUS model in rats, such as a desperate behavior (immobility time in forced swimming, p<0.01), interest lost (sucrose solution preference, p<0.01), activity reduction (autonomous mobility, p<0.01) etc. Meanwhile, tetrandrine (TET) exhibited merely certain amelioration effect on the immobility time in forced swimming (p<0.05) and sucrose solution preference (p<0.05) at a higher dose (60 mg/kg). Furthermore, 5,7-dimethoxy fangchinoline, berbamine, 12-acetoxy berbamine and 12-(4-ethoxy)-butoxy berbamine exhibited no amelioration effect at doses of 30 and 60 mg/kg. In this experiment, as compared with tetrandrine, compounds 1-8 had an evidently suporior amelioration/treatment effect with respect to various indices of CUS model in rats (p<0.01).

By comparison of the range of minimal effective dose, it was shown that compounds 1-8 had an efficacy 8 times higher than that of tetrandrine. It was found that, as compared with tetrandrine, 5,7-dimethoxy fangchinoline, berbamine, 12-acetoxyberbamine and 12-(4-ethoxy)-butoxyberbamine, compounds 1-8 not only had a stronger inhibition effect on GSK-3β activity, but also had a better amelioration effect on depression symptoms such as pleasure lost (anhedonia), despair, mobility reduction and anxiety etc. It was suggested that compounds 1-8 had an unexpected superior anti-depression effect.

Result 2: The influence of the compounds of formula (I) on anxiety behaviors in a CUS depression model in rats was examined by using a well-established elevated plus-maze (EPM) anxiety test procedure.

As shown in the experimental results, the CUS model in rats had obviously decreased percentage of residence time in open arm area and percentage of entry into open arms, as compared with blank control group (p<0.01, see, Table 3). It was suggested that the CUS model rats developed an anxiety behavior. Compounds 1-8 in various dose groups (7.5, 15 and 30 mg/kg) all remarkably increased residence time in open arm area and entries into open arms. Whereas 5,7-dimethoxy-fangchinoline, berbamine, 12-acetoxyberbamine and 12-(4-ethoxy)-butoxyberbamine exhibited no anti-anxiety-like effect at doses of 30 and 60 mg/kg. Although tetrandrine (TET) could increase entries into open arms in a CUS depression model in rats at a higher dose (60 mg/kg), it had no amelioration effect on the residence time in open arms, indicating that tetrandrine could ameliorate an exploratory behavior in a CUS depression model in rats, without amelioration effect on anxiety-like behaviors at a higher dose (60 mg/kg). In this experiment, compounds 1-8 exhibited an anti-anxiety-like effect even at a dose of 7.5 mg/kg, whereas tetrandrine exhibited an amelioration effect on the exploratory behavior in a CUS model in rats merely at a dose of 60 mg/kg. It was suggested that compounds 1-8 had an evidently superior amelioration/treatment effect on anxiety-like behaviors in a CUS model in rats, as compared with tetrandrine, 5,7-dimethoxyfangchinoline, berbamine, 12-acetoxyberbamine and 12-(4-ethoxy)-butoxyberbamine (p<0.01). By comparison of the minimal effective dose, it was shown that compounds 1-8 had a valence which was approximately 8 times higher than that of tetrandrine. It was suggested that compounds 1-8, as represented by the compound YH-200, had an unexpected superior amelioration effect on anxiety symptoms in a patient suffered from depression.

TABLE 3

Influence of the compound of formula (I) on anxiety-like behaviors in a chronic unpredictable stress (CUS) model in rats (Means ± SEM, n = 10).

| Groups | Percentage of residence time in open arms (%) | Percentage of entries into open arms relative to total entries into arms (%) |
|---|---|---|
| Blank control group | 70.2 ± 4.9 | 62.0 ± 2.5 |
| CUS model group | 41.9 ± 3.8** | 37.0 ± 1.6** |
| Model group + Compound 1 | | |
| 7.50 mg/kg | 53.6 ± 4.6##,$$ | 41.2 ± 2.3## |
| 15.0 mg/kg | 60.8 ± 4.0##,$$ | 46.7 ± 3.4## |
| 30.0 mg/kg | 60.6 ± 3.7##,$$ | 53.9 ± 3.5##,$$ |
| Model group + Compound 2 | | |
| 7.50 mg/kg | 56.5 ± 3.0##,$$ | 45.1 ± 3.8## |
| 15.0 mg/kg | 63.6 ± 4.1##,$$ | 49.7 ± 4.0## |
| 30.0 mg/kg | 64.5 ± 3.6##,$$ | 56.2 ± 5.3##,$$ |
| Model group + Compound 3 | | |
| 7.50 mg/kg | 69.1 ± 2.4##,$$ | 57.2 ± 1.8##,$$ |
| 15.0 mg/kg | 72.3 ± 3.6##,$$ | 59.7 ± 2.2##,$$ |
| 30.0 mg/kg | 71.8 ± 3.2##,$$ | 60.2 ± 2.0##,$$ |
| Model group + Compound 4 | | |
| 7.50 mg/kg | 66.2 ± 3.4##,$$ | 54.2 ± 2.6##,$ |
| 15.0 mg/kg | 69.5 ± 4.2##,$$ | 55.3 ± 4.0##,$ |
| 30.0 mg/kg | 68.6 ± 3.2##,$$ | 59.7 ± 5.3##,$$ |
| Model group + Compound 5 | | |
| 7.50 mg/kg | 64.1 ± 3.0##,$$ | 52.7 ± 2.6## |
| 15.0 mg/kg | 67.2 ± 3.1##,$$ | 54.6 ± 3.2##,$ |
| 30.0 mg/kg | 68.4 ± 4.2##,$$ | 60.4 ± 4.6##,$$ |
| Model group + Compound 6 | | |
| 7.5 mg/kg | 59.4 ± 3.3##,$$ | 47.0 ± 2.6## |
| 15 mg/kg | 64.1 ± 3.6##,$$ | 50.5 ± 3.2## |
| 30 mg/kg | 66.0 ± 4.2##,$$ | 57.3 ± 4.6##,$$ |
| Model group + Compound 7 | | |
| 7.5 mg/kg | 54.7 ± 4.1##,$$ | 43.4 ± 2.6## |
| 15 mg/kg | 62.1 ± 3.4##,$$ | 47.9 ± 4.0## |
| 30 mg/kg | 61.5 ± 3.0##,$$ | 54.3 ± 5.6##,$ |
| Model group + Compound 8 | | |
| 7.5 mg/kg | 60.5 ± 3.2##,$$ | 49.2 ± 2.6## |
| 15 mg/kg | 66.1 ± 3.4##,$$ | 51.6 ± 3.1##,$ |
| 30 mg/kg | 67.5 ± 3.8##,$$ | 58.5 ± 4.3##,$$ |

TABLE 3-continued

Influence of the compound of formula (I) on anxiety-like behaviors in a chronic unpredictable stress (CUS) model in rats (Means ± SEM, n = 10).

| Groups | Percentage of residence time in open arms (%) | Percentage of entries into open arms relative to total entries into arms (%) |
|---|---|---|
| Model group + tetrandrine | | |
| 7.5 mg/kg | 42.1 ± 3.7 | 38.0 ± 2.3 |
| 15 mg/kg | 40.6 ± 4.8 | 39.5 ± 3.0 |
| 30 mg/kg | 41.3 ± 3.0 | 43.8 ± 3.2 |
| 60 mg/kg | 42.8 ± 3.5 | 46.2 ± 2.9# |
| Model group + 5,7-dimethoxyfangchinoline | | |
| 30 mg/kg | 43.2 ± 4.1 | 38.9 ± 1.8 |
| 60 mg/kg | 42.8 ± 4.8 | 37.2 ± 1.4 |
| Model group + berbamine | | |
| 30 mg/kg | 41.0 ± 3.0 | 38.3 ± 1.9 |
| 60 mg/kg | 39.6 ± 4.2 | 37.5 ± 1.6 |
| Model group + 12-acetoxyberbamine | | |
| 30 mg/kg | 41.9 ± 3.7 | 38.2 ± 1.8 |
| 60 mg/kg | 43.3 ± 3.4 | 36.8 ± 1.6 |
| Model group + 12-(4-ethoxy)-butoxyberbamine | | |
| 30 mg/kg | 40.1 ± 4.5 | 36.6 ± 1.7 |
| 60 mg/kg | 39.2 ± 3.5 | 37.2 ± 1.3 |
| Imipramine 40 mg/kg | 76.1 ± 1.9##,$$ | 57.1 ± 1.8##,$ |

**$P < 0.01$ as compared with control group;
$P < 0.05$,
$P < 0.01$ as compared with CUS group;
$$P < 0.05$,
$$$P < 0.01$ as compared with tetrandrine 60 mg/kg group.
The data were analyzed by one-way ANOVA test followed by post hoc Student-Newman-Keuls test for multiple comparisons.

Result 3: Sleep disturbance is one of the most common symptoms of neuropsychiatry. From a view of therapeutics, sleep disturbance is one of the most distressful events in patients suffered from nervous diseases and mental illness, especially in depression, and also one of major adverse events that may exacerbate the conditions of nervous disease and mental illness and impede the recovery in patients. For example, patients who are suffering from depression associated with insomnia may have an apparently higher incidence of a suicidal behavior, as compared with a non-insomnia group. Sleep disturbance in nervous and mental diseases can be simulated by using a CUS model in rats. As shown in Table 4, the CUS model in rats exhibited sleep disturbance, which was characterized by indices such as decreased total sleep (TS) and slow wave sleep (SWS) duration, and increased awakening times and rapid eye movements (REM) sleep times, etc. YH-200 (Compound 3) had an evident amelioration effect on the sleep disturbance in the CUS model in rats. Therefore, YH-200 could be useful for treating and ameliorating sleep disturbance in a patient suffering from depression (see, Table 4).

TABLE 4

The amelioration effect of YH-200 (30 mg/kg, p.o.) on sleep in a CUS depression model in rats (Means ± SEM, n = 8).

| | Time (min) | | | |
|---|---|---|---|---|
| | NREM sleep | Deep sleep (SWS) | Rapid eye movement (REM) sleep | Total sleep |
| Day 0 | | | | |
| Normal group | 177.89 ± 16.05 | 40.14 ± 15.17 | 30.20 ± 9.62 | 208.09 ± 23.41 |
| CUS | 172.99 ± 13.63 | 38.36 ± 13.36 | 37.22 ± 4.10 | 210.21 ± 14.44 |
| CUS + YH-200 | 174.44 ± 8.35 | 39.31 ± 10.22 | 37.95 ± 6.28 | 212.40 ± 12.65 |
| Day 21 | | | | |
| Normal group | 170.32 ± 20.86 | 40.46 ± 20.25 | 31.12 ± 3.39 | 201.44 ± 22.24 |
| CUS | 138.50 ± 5.88** | 24.62 ± 3.49** | 22.29 ± 9.14* | 160.79 ± 9.10* |
| CUS + YH-200 | 165.27 ± 7.97# | 48.18 ± 13.77# | 34.06 ± 1.75# | 199.33 ± 9.11# |

REM: rapid eye movement sleep;
NREM: non-REM sleep;
SWS: slow-wave sleep;
TS: total sleep.
*$P < 0.05$, TABLE 4-continued The amelioration effect of YH-200 (30 mg/kg, p.o.) on sleep in a CUS depression model in rats (Means ± SEM, n = 8).

| | Time (min) | | | |
|---|---|---|---|---|
| NREM sleep | Deep sleep (SWS) | Rapid eye movement (REM) sleep | Total sleep | |

\*\*P < 0.01 as compared with blank group;
P < 0.05 as compared with model group (SNK-test).

Example 3

Figure 1:
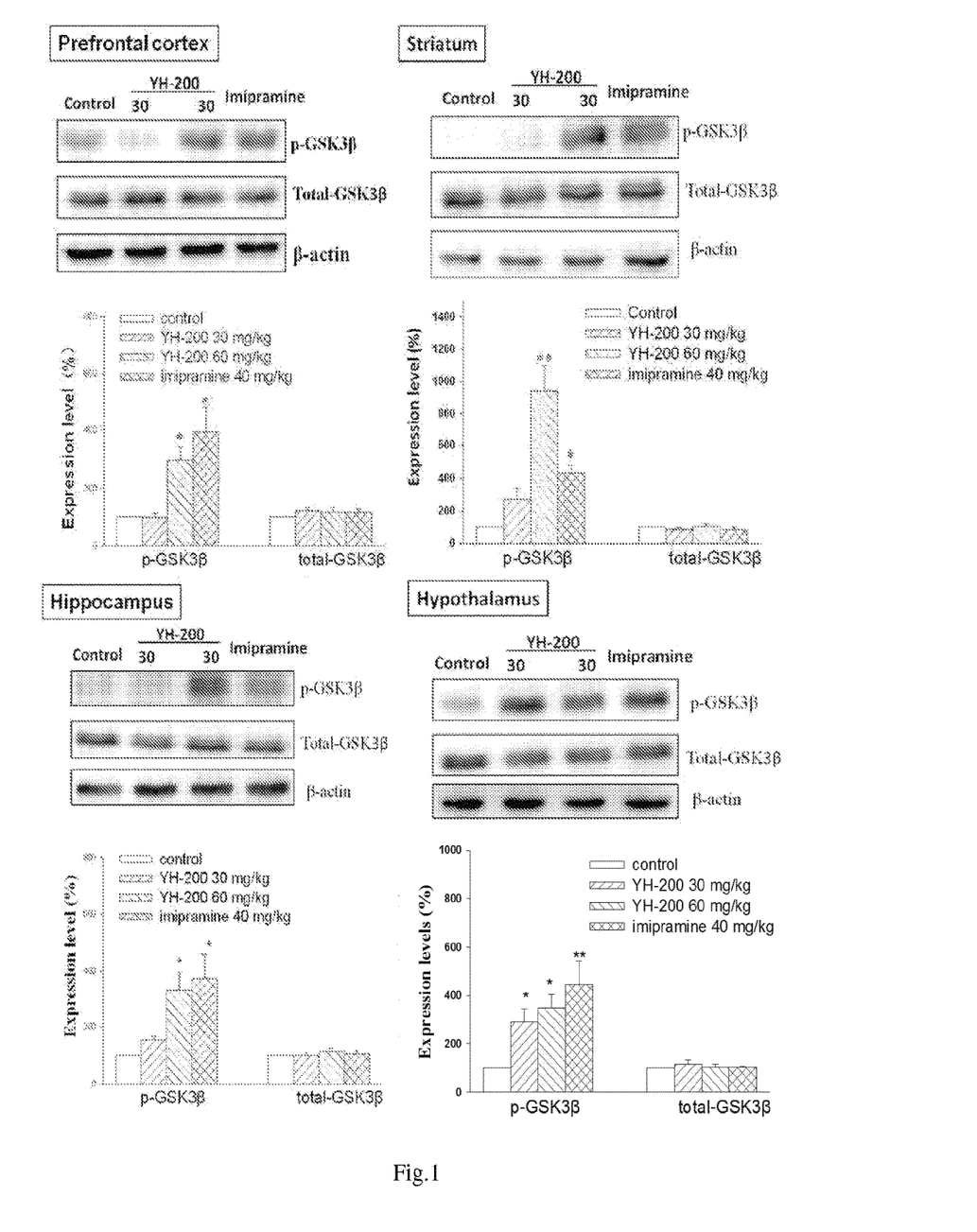
FIG. 1 illustrates the influence of YH-200 (Compound 3) on GSK-3β phosphorylation level in prefrontal lobe cortex, hipocampus, corpus striatum and hypothalamus in mice (Mean±SE, n=4); *P<0.05, **P<0.01 as compared with control group (Student's t-test).

The influence of YH-200 (Compound 3) on GSK-3β phosphorylation level in prefrontal lobe cortex, hipocampus, corpus striatum and hypothalamus in mice (Mean±SE, n=4); *P<0.05, \*\*P<0.01 as compared with control group (Student's t-test)

ICR mice were intragastrically administered of subject medicaments and vehicle. One hour later, brains of those treated mice were obtained after decapitation. Prefrontal lobe cortex, hipocampus, corpus striatum and hypothalamus were isolated and collected respectively. Then protein electrophoresis (Western blot) was carried out with each sample. The results were shown in FIG. 1. Intragastric administration of YH-200 at 30 mg/kg had no evident influence on phosphorylated GSK-3β (p-GSK-3β) and total-GSK-3β in prefrontal lobe cortex, hipocampus and corpus striatum in mice, but resulting in an evidently increased p-GSK-3β level in hypothalamus, as compared with blank control group. However, YH-200, at a dose of 60 mg/kg, resulted in a significantly increased p-GSK-3β level in said four brain sections, but had no influence on the total GSK-3β level.

Example 4

The Relevance of the Anti-Depression Mechanism of YH-200 to the GSK-3β Phosphorylation Level, $5\text{-}HT_{1A}$ and $5\text{-}HT_{2A}$ Receptor A desperate behavior status of human beings may be simulated by an immobility status in a forced swimming model in mice. The mice were put into a cylindrical glass jar (height 20 cm, diameter 10 cm) with a water depth of 15 cm and water temperature of 25±1° C. The mice were allowed to pre-swim for 15 minutes before the experiment, and then were taken out, wiped dry at a warm place, and sent back into cages. In 24 hours, the mice received an intragastric administration; and 60 minutes after the administration, the mice were put into the above-mentioned environment. The accumulative immobility time of the mice in the jar during the 5-minute period of time after six minutes of swimming was measured. A decrease in immobility time was taken as evaluation index.

Figure 2:
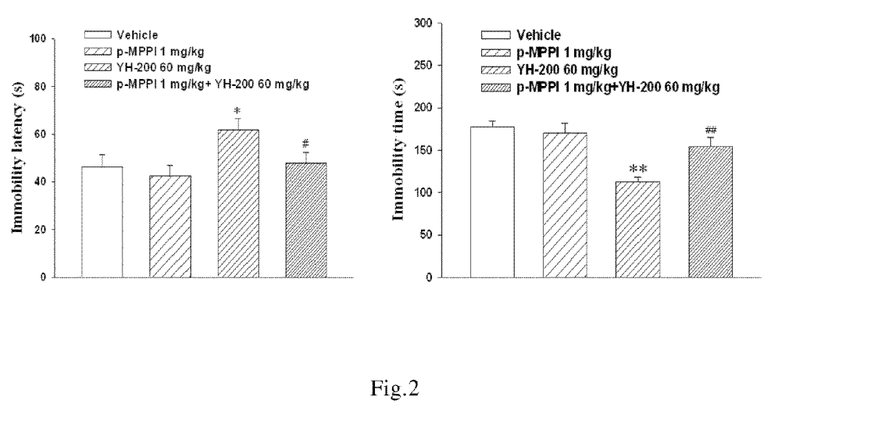
FIG. 2 illustrates that the anti-depression effect of YH-200 (Compound 3) may be inhibited by a 5-HT$_{1A}$ receptor antagonist, pMPPI (Mean±SE, n=12-15).
Figure 3:
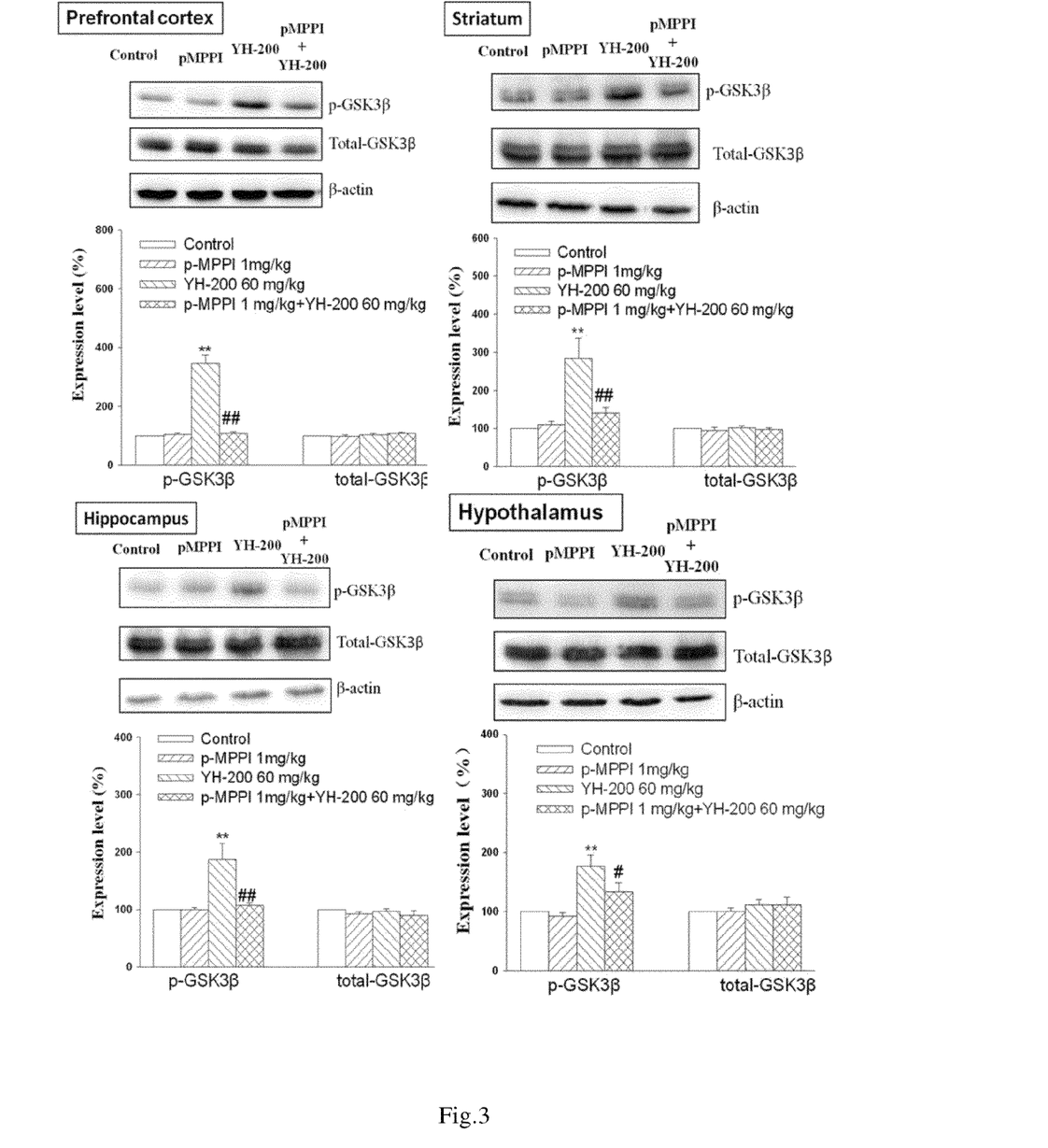
FIG. 3 illustrates that the 5-HT$_{1A}$ receptor antagonist pMPPI may significantly inhibit the YH-200 (Compound 3)-induced enhancement of GSK-3β phosphorylation level in prefrontal lobe cortex, hipocampus, corpus striatum and hypothalamus in mice (Mean±SE, n=6).
Figure 4:
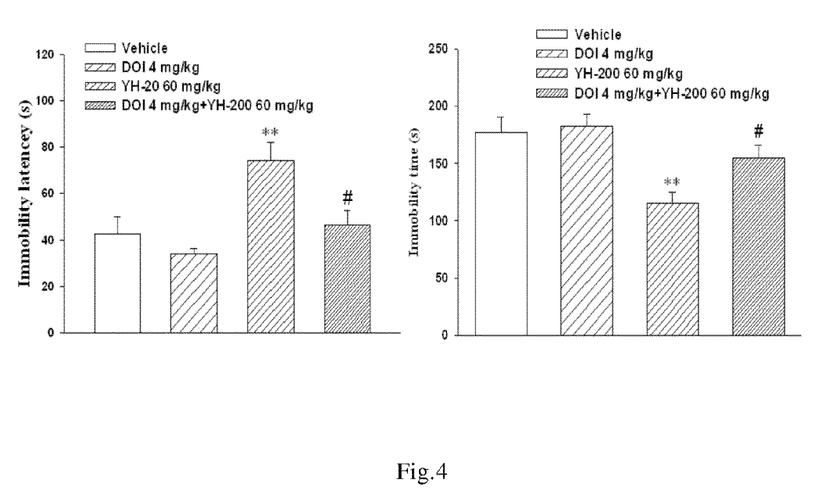
FIG. 4 illustrates that the YH-200 (Compound 3)-induced reduction of immobility time and extension of immobility latency period in mice forced swimming test may be inhibited by a 5-HT$_{2A}$ receptor agonist, DOI (Mean±SE, n=12-15).
Figure 5:
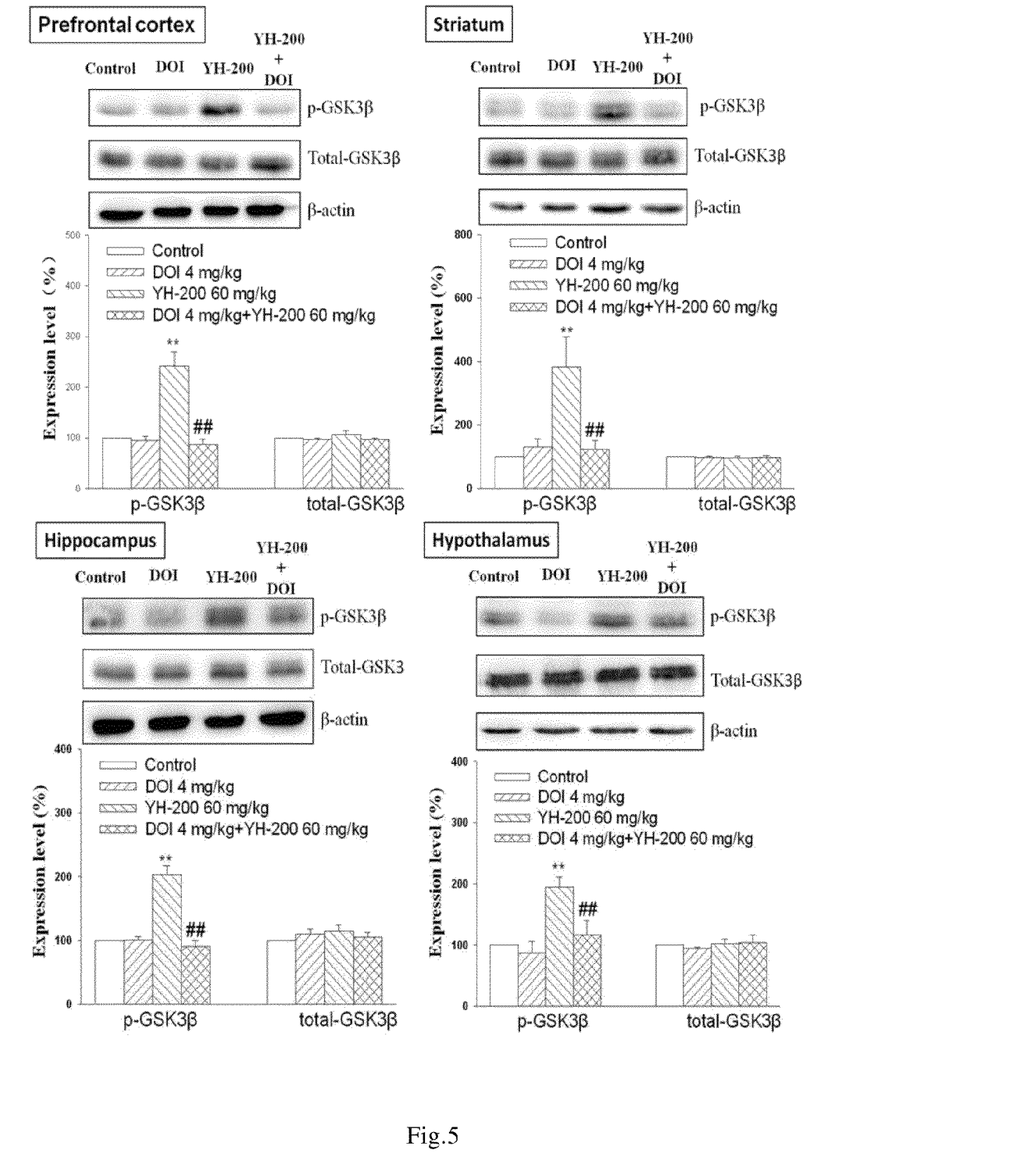
FIG. 5 illustrates that the 5-HT$_{2A}$ receptor agonist, DOI, may inhibit the YH-200 (Compound 3)-induced enhancement of GSK-3β phosphorylation level in prefrontal lobe cortex, hipocampus, corpus striatum and hypothalamus in mice (Mean±SE, n=6).

As shown in the experimental results, compounds 1-8 all exhibited a strong amelioration effect on the immobility latency period and immobility time in swimming, which were representative for desperate behaviors. It was suggested that compounds 1-8 had an amelioration effect on desperate behaviors. As shown in FIG. 2, the anti-depression effect of YH-200 could be inhibited by a $5\text{-}HT_{1A}$ receptor antagonist, pMPPI (Mean±SE, n=12-15). As shown in FIG. 3, an intraperitoneal administration of the $5\text{-}HT_{1A}$ receptor antagonist pMPPI 15 minutes before the intragastric administration of YH-200 could evidently inhibit the YH-200-induced enhancement of GSK-3β phosphorylation level in prefrontal lobe cortex, hipocampus, corpus striatum and hypothalamus in mice (Mean±SE, n=6). As shown in FIG. 4, the YH-200-induced reduction of immobility time and extension of immobility latency period in forced swimming model could be inhibited by a $5\text{-}HT_{2A}$ receptor agonist, DOI (Mean±SE, n=12-15). As shown in FIG. 5, the $5\text{-}HT_{2A}$ receptor agonist DOI inhibited the YH-200 induced enhancement of GSK-3β phosphorylation level in prefrontal lobe cortex, hipocampus, corpus striatum and hypothalamus in mice (Mean±SE, n=6). It was thus deduced that the anti-depression effect of YH-200 might be relevant to the enhancement of $5\text{-}HT_{1A}$ receptor function, the inhibition of $5\text{-}HT_{2A}$ receptor activity, and the enhancement of GSK-3β phosphorylation level of YH-200. In the figures: *P<0.05, \*\*P<0.01 as compared with control group; #P<0.05, ##P<0.05 as compared with YH-200 (60 mg/kg) group. The data were analyzed by one-way ANOVA test followed by post hoc Student-Newman-Keuls test for multiple comparisons.

Example 5

The influence of compounds 1-8 and tetrandrine by intragastric administration for consecutive 14 days on aspartate transaminase (also called aspartate aminotransferase, AST) and alanine transaminase (also called alanine aminotransferase, ALT) in mice.

The mice were administered with compounds 1-8 and tetrandrine for consecutive 14 days. Blood was collected from epicanthal, stood at room temperature for about 2 hours, and centrifuged for 12 minutes at 3000 r/min after coagulation. The serum was removed and centrifuged again. Alanine transaminase (ALT) and aspartate transaminase (AST) levels were determined

TABLE 5

The influence of intragastric administration for consecutive 14 days on AST, ALT and AST/ALT in serum of mice (Means ± SEM, n = 10)

| Compound | Dose (mg/kg/day) | AST (U/L) | ALT (U/L) | AST/ALT |
|---|---|---|---|---|
| Blank control | — | 91.8 ± 12.9 | 77.8 ± 18.1 | 1.18 ± 0.24 |
| Compound 1 | 60 | 117.7 ± 16.1 | 80.9 ± 21.4 | 1.45 ± 0.21 |
| Compound 2 | 60 | 108.4 ± 17.4 | 87.2 ± 24.7 | 1.24 ± 0.26 |

TABLE 5-continued

The influence of intragastric administration for consecutive 14 days on AST, ALT and AST/ALT in serum of mice (Means ± SEM, n = 10)

| Compound | Dose (mg/kg/day) | AST (U/L) | ALT (U/L) | AST/ALT |
|---|---|---|---|---|
| Compound 3 | 60 | 102.3 ± 14.5 | 82.1 ± 16.4 | 1.25 ± 0.18 |
| Compound 4 | 60 | 88.6 ± 20.3 | 79.5 ± 19.1 | 1.11 ± 0.25 |
| Compound 5 | 60 | 101.5 ± 18.7 | 91.7 ± 15.5 | 1.11 ± 0.19 |
| Compound 6 | 60 | 99.4 ± 21.1 | 92.3 ± 21.2 | 1.08 ± 0.27 |
| Compound 7 | 60 | 93.6 ± 17.8 | 82.4 ± 17.9 | 1.14 ± 0.20 |
| Compound 8 | 60 | 89.2 ± 16.7 | 80.1 ± 21.3 | 1.11 ± 0.21 |
| tetrandrine | 30 | 204.8 ± 21.8** | 83.8 ± 15.9 | 2.44 ± 0.21** |
|  | 60 | 205.6 ± 22.8** | 113.2 ± 20.6* | 1.82 ± 0.26* |

*P < 0.05 and
**P < 0.01 as compared with control group (Student's t-test).

Usually, aspartate transaminase (AST) and alanine transaminase (ALT) are present in hepatocytes. They enter into blood when the hepatocytes are impaired, thus enhancing the level thereof in blood serum. Therefore, the activities of aspartate transaminase (AST) and alanine transaminase (ALT) and the ratio thereof could reflect the extent of hepatic impairment. The inventors found that (see, Table 5), there was no evident change in aspartate transaminase (AST) activity, alanine transaminase (ALT) activity and the ratio thereof (AST/ALT) in blood serum after an intragastric administration of compounds 1-8 (60 mg/kg) for consecutive 14 days; meanwhile, as a result from an intragastric administration of tetrandrine for consecutive 14 days, the aspartate aminotransferase (AST) activity, the alanine transaminase (ALT) activity and the ratio thereof (AST/ALT) were all evidently enhanced by tetrandrine at a dose of 60 mg/kg, as compared with control group (P<0.01). Moreover, the aspartate transaminase (AST) activity (P<0.01) and the AST/ALT ratio (P<0.05) were evidently enhanced by tetrandrine at a dose of 30 mg/kg. It proved that, with respect to liver, compounds 1-8 were safer than tetrandrine.

Example 6

Preparation of Compounds 4 and 5

1 eq. of Compound 3 (YH-200) was dissolved in $CF_3COOH$ and added with $H_2O$ (q.s.). The reaction was boiled under reflux at 100° C., added with $Br_2$-containing $CH_3COOH$ solution dropwise (done within 20 minutes), and then carried on for 1 h at 100° C. The reaction solution was poured into ice water, neutralized with saturated concentrated aqueous ammonia, and extracted by $CHCl_3$. The phase of $CHCl_3$ was dried under anhydrous sodium sulfate, condensed and separated via column chromatography ($CH_2Cl_2$/MeOH 10/1), giving a light yellow solid. Compound 4 was obtained if $Br_2$ was added at the same equivalent concentration as the YH-200; and Compound 5 was obtained if $Br_2$ was added at a double-equivalent concentration.

What is claimed is:

1. A method of alleviating and/or treating depression, comprising the step of administering to a subject in need thereof a therapeutically effective amount of a compound of formula (I) or a pharmaceutically acceptable salt thereof, formula (I)

wherein, $R_1$ is an alkyl of formula —$C_nH_{2n+1}$, wherein n is an integer greater than or equal to 1 and smaller than or equal to 6;

$R_2$ is selected from the group consisting of hydrogen, methyl, ethyl, propyl, isopropyl, butyl, isobutyl and acyl;

$X_1$, $X_2$, $X_3$ and $X_4$ may be the same or different, and each independently represent hydrogen, fluorine, chlorine, bromine, iodine, nitro, hydroxyl or methoxy; and when n is 1, $X_1$, $X_2$, $X_3$ and $X_4$ may not all be hydrogen.

2. The method of claim 1, wherein $R_1$ is methyl, and at least one of $X_1$, $X_2$, $X_3$ and $X_4$ represents fluorine, chlorine, bromine, iodine or nitro.

3. The method of claim 1, wherein $R_1$ is methyl, and $X_1$ and $X_3$ each independently represent chlorine or bromine.

4. The method of claim 1, wherein $R_1$ is methyl, and $X_1$ and $X_3$ are the same and represent chlorine or bromine.

5. The method of claim 3, wherein $R_2$ is methyl.

6. The method of claim 1, wherein n is 2, 3 or 4.

7. The method of claim 6, wherein $R_2$ is methyl.

8. The method of claim 1, wherein the compound of formula (I) is selected from the group consisting of 5-chloro-7-methoxy fangchinoline (Compound 1), 5,14-dibromo-7-methoxy fangchinoline (Compound 2), 7-ethoxy fangchinoline (Compound 3), 5-bromo-7-ethoxy fangchinoline (Compound 4), 5,14-dibromo-7-ethoxy fangchinoline (Compound 5), 7-propoxy fangchinoline (Compound 6), 7-butoxy fangchinoline (Compound 7), and 7-isopropoxy fangchinoline (Compound 8).

9. A compound of formula (I) or a pharmaceutically acceptable salt thereof, formula (I)

wherein,
$R_1$ is ethyl;
$R_2$ is methyl;
$X_1$, $X_2$, $X_3$ and $X_4$ may be the same or different, each independently represent hydrogen, fluorine, chlorine, bromine, iodine, nitro, hydroxyl or methoxy, and $X_1$, $X_2$, $X_3$ and $X_4$ may not all be hydrogen.

10. The compound or a pharmaceutically acceptable salt thereof of claim 9, wherein $X_1$ and $X_3$ each independently represent fluorine, chlorine, bromine, iodine or nitro.

11. The compound or a pharmaceutically acceptable salt thereof of claim 9, wherein $X_1$ and $X_3$ each independently represent chlorine or bromine.

12. The compound or a pharmaceutically acceptable salt thereof of claim 9, wherein $X_1$ and $X_3$ are the same and represent chlorine or bromine.

13. The compound or a pharmaceutically acceptable salt thereof of claim 9, wherein the compound of formula (I) is selected from the group consisting of 5-bromo-7-ethoxy fangchinoline (Compound 4) and 5,14-dibromo-7-ethoxy fangchinoline (Compound 5).

14. A method of alleviating and/or treating schizophrenia, comprising the step of administering to a subject in need thereof a therapeutically effective amount of a compound of formula (I) or a pharmaceutically acceptable salt thereof, formula (I)

wherein,
$R_1$ is an alkyl of formula —$C_nH_{2n+1}$, wherein n is an integer greater than or equal to 1 and smaller than or equal to 6;
$R_2$ is selected from the group consisting of hydrogen, methyl, ethyl, propyl, isopropyl, butyl, isobutyl and acyl;
$X_1$, $X_2$, $X_3$ and $X_4$ may be the same or different, and each independently represent hydrogen, fluorine, chlorine, bromine, iodine, nitro, hydroxyl or methoxy; and
when n is 1, $X_1$, $X_2$, $X_3$ and $X_4$ may not all be hydrogen.

15. The method of claim 14, wherein the compound of formula (I) is selected from the group consisting of 5-chloro-7-methoxy fangchinoline (Compound 1), 5,14-dibromo-7-methoxy fangchinoline (Compound 2), 7-ethoxy fangchinoline (Compound 3), 5-bromo-7-ethoxy fangchinoline (Compound 4), 5,14-dibromo-7-ethoxy fangchinoline (Compound 5), 7-propoxy fangchinoline (Compound 6), 7-butoxy fangchinoline (Compound 7), and 7-isopropoxy fangchinoline (Compound 8).

* * * * *